(12) United States Patent
Wang et al.

(10) Patent No.: US 9,206,465 B2
(45) Date of Patent: Dec. 8, 2015

(54) METHODS, COMPOSITIONS, AND KITS FOR DETECTING PROTEASE ACTIVITY IN COMPLEX SAMPLES

(71) Applicant: BioResource International, Inc., Durham, NC (US)

(72) Inventors: Jeng-Jie Wang, Apex, NC (US); Bonnye Talbot, Durham, NC (US); Steven Kaczowka, Durham, NC (US)

(73) Assignee: BioResource International, Inc., Durham, NC (US)

( * ) Notice: Subject to any disclaimer, the term of this patent is extended or adjusted under 35 U.S.C. 154(b) by 0 days.

(21) Appl. No.: 14/204,531

(22) Filed: Mar. 11, 2014

(65) Prior Publication Data

US 2014/0255965 A1    Sep. 11, 2014

Related U.S. Application Data

(60) Provisional application No. 61/775,947, filed on Mar. 11, 2013.

(51) Int. Cl.
*C12Q 1/37*   (2006.01)

(52) U.S. Cl.
CPC .......................................... *C12Q 1/37* (2013.01)

(58) Field of Classification Search
IPC .......................................................... C12Q 1/37
See application file for complete search history.

(56) References Cited

U.S. PATENT DOCUMENTS

| 5,786,137 | A | 7/1998 | Diamond |
| 6,190,905 | B1 | 2/2001 | Dalboge |
| 7,608,444 | B2 | 10/2009 | Oestergaard et al. |
| 2006/0259995 | A1 | 11/2006 | Cayouette |
| 2012/0264153 | A1 | 10/2012 | Yu |

FOREIGN PATENT DOCUMENTS

WO    2013026796 A1    2/2013

OTHER PUBLICATIONS (Novex® Zymogram Gels, Life Technologies, Life Technologies Protocols, Publication No. IM-6006, 2004, http://www.lifetechnologies.com/us/en/home/references/protocols/proteins-expression-isolation-and-analysis/protein-gel-electrophoresis/novex-zymogram-gels.html).*

Zymogram Development Buffer, Bio-Rad, undated ref.—http://www.bio-rad.com/evportal/evolutionPortal.portal?_nfpb=true&_pageLabel=search_page&sfMode=search&sfStartNumber=1&clearQR=true&js=1&searchString=Zymogram%20development%20buffer&database=productskus+productcategories+productdetails+msds+literatures+inserts+faqs+downloads+webpages+assays+genes+pathways+plates+promotions&tabName=DIVISION.*

(Continued)

*Primary Examiner* — Rosanne Kosson
(74) *Attorney, Agent, or Firm* — NK Patent Law, PLLC (57) ABSTRACT

Methods and kits are provided for measuring protease activity in samples such as feed or food samples. The methods include adding a water insoluble substrate with a signal producing group to a feed or food sample containing the protease activity to be measured, incubating the sample in phosphate-free buffer such that the signal is produced, and measuring the amount of protease activity in the sample. The methods do not require separation of the incubation buffer from the feed or food and allow for visual inspection of a colorimetric signal for a semi-quantitative measurement of the in-feed/in-food protease activity. Thus, the assay is advantageous as it can be performed on-site without the use of laboratory equipment.

11 Claims, 6 Drawing Sheets

(56) References Cited

OTHER PUBLICATIONS

Megazyme, Assay of Endo-protease Using Protazyme AK Tablets, 2008, http://secure.megazyme.com/files/Booklet/T-PRAK_0811_DATA.pdf.*

Toth et al., "Assessment of gelatinases (MMP-2 and MMP-9) by gelatin zymography," Methods Mol Med 57:1-10, 2001.*

International Search Report dated Jun. 6, 2014 for application PCT/US2014/023222 filed Mar. 11, 2013.

Megazyme website page visited Feb. 2012, titled "Frequently Asked Questions, Protazyme AK Tablets," http://www.megazyme.com/downloads/en/faq/T-PRAK.pdf.

* cited by examiner

METHODS, COMPOSITIONS, AND KITS FOR DETECTING PROTEASE ACTIVITY IN COMPLEX SAMPLES

CROSS REFERENCE TO RELATED APPLICATIONS

This application claims the benefit of U.S. Provisional Patent Application No. 61/775,947 filed Mar. 11, 2013, the disclosure of which is hereby incorporated by reference in its entirety. This application is related to International Patent Application No. PCT/US14/23222 filed Mar. 11, 2014, the disclosure of which is hereby incorporated by reference in its entirety.

TECHNICAL FIELD

The present disclosure relates to a method for detecting protease activity in a complex sample. Particularly, the present disclosure relates to a method for detecting protease activity in a feed or in a food sample.

BACKGROUND

Proteases are commonly added to animal feed in order to increase the protein digestibility of the feed. In some cases, the protease is added to the feed prior to the pelleting process, which involves heating the feed mixture to high temperatures (70° C.-95°+C). In other instances, the protease enzyme is sprayed onto and/or mixed into the feed. Either way, it is often desirable to measure the amount of protease activity in the feed product to make sure that the protease was in fact added, that the protease was added in the correct quantity, and that the protease survived the pelleting and/or mixing process.

Numerous methods are known for the detection of protease activity in samples and the methods are often based on the use of natural protein substrates, synthetic peptide substrates, or peptide analog substrates labeled with a chromophore, a flurophore, or a radioisotope to detect the protease activity. However, the problem in measuring protease activity that has been added to feed products is that naturally occurring components of feed, including endogenous protein substrates in the feed, can compete with the labeled substrate being used to detect and measure the protease activity. This issue creates a significant challenge to testing protease activity in feed.

For example, PROTAZYME AK tablets from MEGA-ZYME, INC. are useful for quantifying the activity of pure proteases such as VERSAZYME (BIORESOURCE INTERNATIONAL, INC.), RONOZYME PROACT (RONOZYME, INC.), and AXTRA 102 TPT XAP (DANISCO, INC.) prior to addition as feed additives. However, the manufacture acknowledges the limitations of using the PROTAZYME AK substrate to measure protease activity once it has been added to feed (see http://secure.megazyme.com/files/FAQ%27s/T-PRAK1000__1204_FAQ.pdf). In an attempt to get around the issue of the feed inhibiting the protease activity measurement, existing methods require steps to first extract the added protease from the feed and to then separate the insoluble feed from the protease-containing soluble extract. The extraction and separation steps add a level of complexity to the in-feed assay that results in the need for sophisticated equipment such as for example a grinder, a micropipettor, a spectrophotometer, and a centrifuge. The use of such equipment increases the cost of the assay and also usually requires the sample to be sent out from the feed-processing facility to a laboratory that is set up to perform the assay. This then dramatically increases the time needed to obtain the test results.

Accordingly, there remains an unmet need for an in-feed/in-food protease assay that can be performed on-site and without the need for sophisticated equipment. The presently disclosed subject matter provides such an assay.

SUMMARY

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

In one aspect, methods are provided for measuring protease activity in a feed or a food sample including adding a substrate for a protease to the sample having the protease activity to be measured, wherein the substrate is insoluble in aqueous solution and has a polypeptide attached to a signal producing group such that the signal is produced upon cleavage of the polypeptide by the protease; and incubating the substrate with the sample in a reaction buffer essentially free of phosphate under conditions that allow for cleavage of the polypeptide such that the signal is produced for measurement of the protease activity.

In one aspect, methods are provided for measuring protease activity in a feed or a food sample consisting of adding a substrate for a protease to the sample that has the protease activity to be measured, wherein the substrate is insoluble in aqueous solution and has a polypeptide attached to a signal producing group such that the signal is produced upon cleavage of the polypeptide by the protease; mixing the substrate with the sample one or more times; incubating the substrate with the sample in a reaction buffer essentially free of phosphate under conditions that allow for cleavage of the polypeptide such that the signal is produced for measurement of the protease activity; and qualitatively, semi-quantitatively, or quantitatively measuring the protease activity by the amount of the signal that is produced.

In one aspect, kits are provided for measuring protease activity in a feed or a food sample including a substrate for a protease activity to be measured, wherein the substrate is insoluble in aqueous solution and has a polypeptide attached to a signal producing group such that the signal is produced upon cleavage of the polypeptide by the protease; a reaction buffer essentially free of phosphate; and an instruction manual for incubating the substrate with the sample having the protease activity to be measured in the reaction buffer essentially free of phosphate under conditions that allow for cleavage of the polypeptide such that the signal is produced for measurement of the protease activity.

In one aspect, kits are provided for measuring protease activity in a feed or a food sample including 1) a substrate for a protease activity to be measured, wherein the substrate is insoluble in aqueous solution and has a polypeptide attached to a signal producing group such that the signal is produced upon cleavage of the polypeptide by the protease; 2) a reaction buffer essentially free of phosphate; and 3) an instruction manual for incubating the substrate with a feed sample having the protease activity to be measured, the instruction manual consisting of the steps of adding the substrate for the protease to the feed sample; mixing the substrate with the feed sample one or more times; incubating the substrate with the feed sample in the reaction buffer essentially free of phosphate under conditions that allow for cleavage of the polypeptide such that the signal is produced for measurement of the protease activity; and qualitatively, semi-quantitatively, or quantitatively measuring the protease activity by the amount of the signal that is produced.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

FIG. 3A shows the visual response with 10 mg substrate, FIG. 3B shows the linear absorbance response with 25 mg substrate, FIG. 3C shows the linear absorbance response with 50 mg substrate, and FIG. 3D shows the linear absorbance response with 100 mg substrate.

DETAILED DESCRIPTION

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

Unless otherwise defined, all technical terms used herein have the same meaning as commonly understood by one of ordinary skill in the art to which this disclosure belongs.

Figure 1:
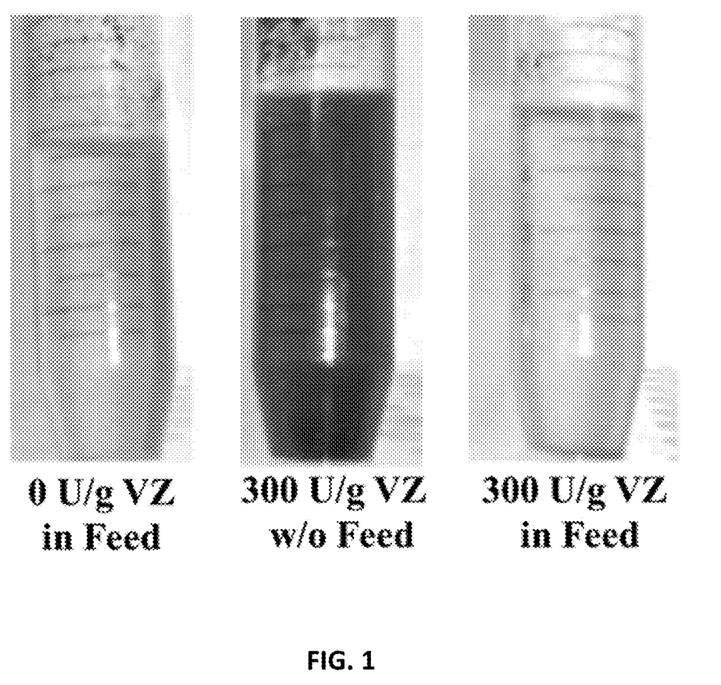
FIG. 1 is a photograph showing measurement of protease activity in 200 mM Na—PO$_4$ buffer, pH9.0 in the presence and absence of feed using an insoluble protein substrate comprising casein linked to azurine. The sample labeled "0 U/g VZ in feed" is a sample containing feed without added protease enzyme, the sample labeled "300 U/g VZ w/o Feed" is a sample without feed containing ~300 U/g protease enzyme, and the sample labeled "300 U/g VZ in Feed" is a sample containing feed spiked with ~300 U/g protease enzyme.
Figure 2:
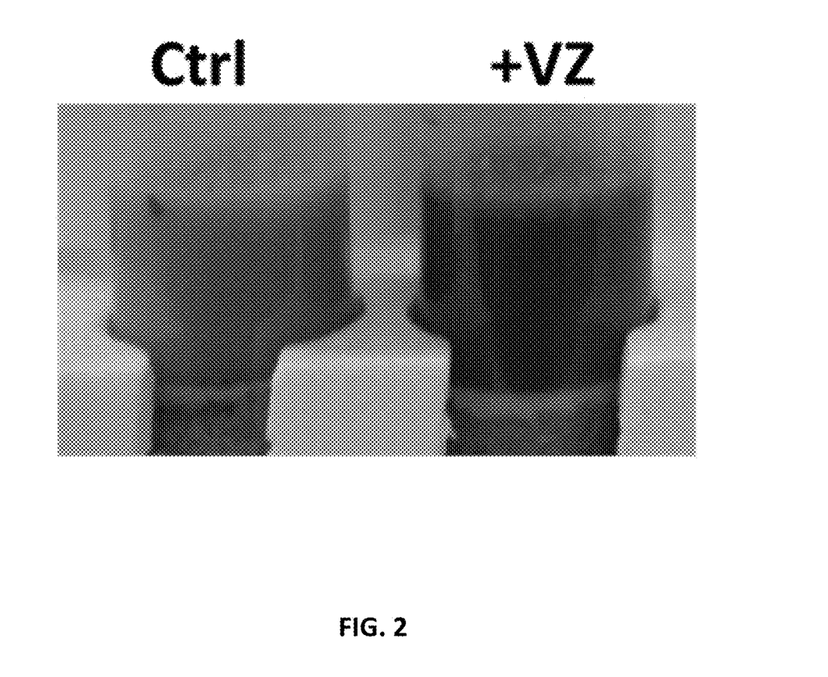
FIG. 2 is a photograph of the same protease activity assay shown in FIG. 1 except that the phosphate buffer was replaced with 200 mM Tri-Cl pH9.0 buffer. The sample labeled "Ctrl" is feed without any added protease enzyme and the sample labeled "VZ" is the same feed spiked with ~1,000 U/g protease enzyme.

The present inventors discovered the unexpected result that phosphate buffer widely used to measure protease activity can interfere with the activity measurement in the presence of feed samples. The present inventors discovered that protease activity could, however, be measured in the presence of feed when the buffer used was free of phosphate. These striking results are shown in FIGS. 1 and 2 below. FIG. 1 shows protease activity (300 U/g VZ) measured in the presence and absence of feed in a phosphate containing buffer. The sample labeled "0 U/g VZ in feed" is a sample containing feed without added protease enzyme, the sample labeled "300 U/g VZ w/o Feed" is a sample without feed containing ~300 U/g protease enzyme, and the sample labeled "300 U/g VZ in Feed" is a sample containing feed spiked with ~300 U/g protease enzyme. As can be seen in FIG. 1, there appears to be close to a complete absence of protease activity in the sample containing feed, whereas there is a large amount of protease activity in the sample without feed.

Prior to the discovery disclosed herein, the negative results observed in the presence of feed (as exemplified in FIG. 1) were believed to be due to competition of endogenous protein substrates in the feed. The results shown in FIG. 2 indicate that this is not the case. FIG. 2 shows the results for the protease activity assay shown in FIG. 1 except that the phosphate buffer was replaced with 200 mM Tri-Cl pH9.0 buffer. The sample labeled "Ctrl" is feed without any added protease enzyme and the sample labeled "VZ" is the same feed spiked with ~1,000 U/g protease enzyme. Surprisingly, and unlike for use of a phosphate buffer, the Tris buffer results in an easily identifiable positive signal for protease activity (+VZ) in the presence of feed as can be seen in FIG. 2. In addition, a significant reduction in the protease activity reaction signal was observed when a small quantity of phosphate (2.5% Na—PO$_4$ buffer) was added to the Tris buffer in the same reaction described for FIG. 2 (results not shown). The reaction signal decreased visibly in the presence of even the small amount of phosphate buffer.

As a result of this finding, the present disclosure provides methods for measuring protease activity in a feed or a food sample in reaction buffers essentially free of phosphate. The methods, compositions, and kits of the present disclosure are described in further detail below.

DEFINITIONS

The term "sample" for the purposes of the specification and claims is intended to mean any sample containing a protease activity to be measured. Exemplary samples include, but are not limited to, complex samples such as feed samples, food samples, feed ingredient samples, feed component samples, food component samples, fermentation broth samples, and cell culture medium samples. In addition, for the purposes of the specification and claims, the terms "feed", "food", "feed sample", and "food sample", are herein used interchangeably. Similarly, and for the purposes of the specification and claims, the terms "in-feed assay" and "in-food assay" are herein used interchangeably.

The term "protease" for the purposes of the specification and claims is intended to mean any protease enzyme. In one aspect, the protease is of a type of protease that is used in the agricultural industry as an animal feed additive to improve the digestibility of the feed. Exemplary feed additive proteases of the present disclosure include, but are not limited to, VERSAZYME protease from BIORESOURCE INTERNATIONAL, INC., RONOZYME PROACT protease from DSM, INC., and AXTRA 102 TPT XAP protease from DANISCO, INC.

For the purposes of the specification and claims, the "substrates" of the presently disclosed subject matter are insoluble in aqueous solution and include a polypeptide attached to a signal producing group such that the signal is produced upon cleavage of the polypeptide by the protease that is being measured. The term "polypeptide" is used in its broadest sense and for the purposes of the specification and claims includes, peptides, polypeptides, and proteins, as well as peptides, polypeptides, and proteins that contain one or more non-natural amino acids or any other chemical modification that allows the polypeptide to function as a substrate for the protease enzyme whose activity is being measured. The "signal producing group" of the "substrate" can be attached to the "polypeptide" by any means, including by covalent or non-covalent means, such that a signal can be produced by the signal producing group upon cleavage of the polypeptide while present in the "sample" by the protease that is being measured. In one example, the signal producing group is attached to the polypeptide by crosslinking. Signal producing groups of the insoluble protease substrates of the present disclosure include, for example, chromophores, flurophores, and radioisotopes capable of producing a signal upon cleavage of the polpeptide by the protease that can be measured in the sample. Specific signal producing groups of the present disclosure include, for example, Azo dye, Remazol Brilliant Blue, p-Nitroaniline, and Iodine-125. Exemplary substrates of the present disclosure include, but are not limited to, Azurine crosslinked casein and Gelatin casein—Remazol Brilliant Blue. Insoluble protease substrates that contain a signal producing group that produces a color change upon cleavage of the substate can be useful with the in-feed protease assay for both semi-quantitative visual inspection and for generating quantitative results by reading absorbance with a spectrophotometer.

For purposes of the specification and claims, the phrase "reaction buffer essentially free of phosphate" is intended to mean that the reaction buffer is not a phosphate based buffer and exogenous phosphate has not been added to the reaction buffer. For example, the phrase "essentially free of phosphate" was not intended to exclude reaction buffer that might contain trace amounts of phosphate.

In one aspect of the present disclosure, methods are provided for measuring protease activity in a feed or a food sample including adding a substrate for a protease to the sample having the protease activity to be measured, wherein the substrate is insoluble in aqueous solution and has a polypeptide attached to a signal producing group such that the signal is produced upon cleavage of the polypeptide by the protease; and incubating the substrate with the sample in a reaction buffer essentially free of phosphate under conditions that allow for cleavage of the polypeptide such that the signal is produced for measurement of the protease activity. In the method, the feed can be an animal feed and the protease can be a type of protease that is added to the animal feed to improve the protein digestability of the feed.

In the method for measuring protease activity in a feed or a food sample, the polypeptide can be casein and the signal producing group can be one of a chromophore, a flurophore, or a radioisotope. The signal producing group can be a chromophore, and the protease activity can be measured by visual inspection of a color change resulting from the signal produced by the chromophore. The measuring of the protease activity can be a semiquantitative measurement made through comparison of the signal produced by the chromophore to the signal produced by the chromophore in a standard curve of one or more of the feed samples comprising a known amount of the protease. In the method, the polypeptide can be casein and the signal producing group can be azurine or Remazol Brilliant Blue.

In one aspect, the method for measuring protease activity in a feed or a food sample can further include mixing the feed sample and the substrate one or more times during the incubation. In the method, the buffer can include about 1% to 15% of an ionic detergent. In the method, the animal feed can be a pelleted feed and the buffer can include about 5% to 10% sodium dodecyl sulfate (SDS). In the method, the reaction buffer can have a pH range between about pH6.5 to pH11 or a pH range between about pH7 to pH9. In the method, the reaction buffer can be a Tris buffer at a pH of about pH7 to pH9. In the method, the conditions that allow for cleavage of the polypeptide can be incubation at a temperature ranging from about 30° C. to 65° C. for a time period ranging from 30 minutes to 5 hours.

In one aspect of the method for measuring protease activity in a feed or a food sample, the feed can be animal feed, and the protease can be a type of protease that is added to the animal feed to improve the protein digestability of the feed, the polypeptide can be casein and the signal producing group can a chromophore, the reaction buffer an be a Tris buffer at a pH of about pH7 to pH9 having about 1% to 15% SDS, and the conditions that allow for cleavage of the polypeptide can be incubation at a temperature ranging from about 30° C. to 65° C. for a time period ranging from 30 minutes to 5 hours. The method can further include measuring the protease activity by visual inspection of a color change resulting from the signal produced by the chromophore.

Thus, the present methods do not require centrifugation or filtration of the sample to separate the reaction buffer from the feed or food sample in order to obtain a measurement of the protease activity in the sample. This allows for the assay to be performed without the use of expensive equipment. In addition, the present methods for measuring protease activity can be performed at the site of feed/food processing, obviating the need to ship the samples off-site for analysis and, thus, avoiding lengthy delays in obtaining sample results.

In another aspect of the present disclosure, methods are provided for measuring protease activity in a feed or a food sample consisting solely of the steps of 1) adding a substrate for a protease to the sample that has the protease activity to be measured, wherein the substrate is insoluble in aqueous solution and has a polypeptide attached to a signal producing group such that the signal is produced upon cleavage of the polypeptide by the protease; 2) mixing the substrate with the sample one or more times; 3) incubating the substrate with the sample in a reaction buffer essentially free of phosphate under conditions that allow for cleavage of the polypeptide such that the signal is produced for measurement of the protease activity; and 4) qualitatively, semi-quantitatively, or quantitatively measuring the protease activity by the amount of the signal that is produced.

In another aspect of the present disclosure, kits are provided for measuring protease activity in a feed or a food sample, the kits including: 1) a substrate for a protease activity to be measured, wherein the substrate is insoluble in aqueous solution and has a polypeptide attached to a signal producing group such that the signal is produced upon cleavage of the polypeptide by the protease; 2) a reaction buffer essentially free of phosphate; and 3) an instruction manual for incubating the substrate with the sample having the protease activity to be measured in the reaction buffer essentially free of phosphate under conditions that allow for cleavage of the polypeptide such that the signal is produced for measurement of the protease activity. The feed can be an animal feed and the protease can be a type of protease that is added to the animal feed to improve the protein digestability of the feed.

The kits can further include one or more tubes for the incubation. In one aspect of the kit, the signal producing group can be a chromophore and the instruction manual can further include instructions for measuring the protease activity by visual inspection of a color change resulting from the signal produced by the chromophore. The polypeptide in the kit can be casein and the signal producing group can be one of a chromophore, a flurophore, or a radioisotope. The polypeptide in the kit can be casein and the signal producing group can be azurine or Remazol Brilliant Blue.

In one aspect of the kit, the instruction manual can further include instructions for measuring the protease activity in a semiquantitative manner through comparison of the signal produced by the chromophore to the signal produced by the chromophore in a standard curve of one or more of the feed samples comprising a known amount of the protease. The kit instruction manual can further include instructions for mixing the feed sample and the substrate one or more times during the incubation.

In the kit, the reaction buffer can include about 1% to 15% of an ionic detergent. The animal feed can be a pelleted feed and the reaction buffer in the kit can include about 5% to 10% sodium dodecyl sulfate (SDS). The reaction buffer in the kit can have a pH range between about pH6.5 to pH11 or between about pH7 to pH9. The reaction buffer in the kit can be a Tris buffer at a pH of about pH7 to pH9. In one aspect of the kit, the conditions that allow for cleavage of the polypeptide can be incubation at a temperature ranging from about 30° C. to 65° C. for a time period ranging from 30 minutes to 5 hours.

In one aspect of the kit, the feed can be an animal feed, the protease can be a type of protease that is added to the animal feed to improve the protein digestability of the feed, the polypeptide can be casein and the signal producing group can be a chromophore, the reaction buffer can be a Tris buffer at a pH of about pH7 to pH9 having about 1% to 15% SDS, and the conditions that allow for cleavage of the polypeptide can be incubation at a temperature ranging from about 30° C. to 65° C. for a time period ranging from 30 minutes to 5 hours. The kit can further include instructions for measuring the protease activity by visual inspection of a color change resulting from the signal produced by the chromophore.

In one aspect, kits are provided for measuring protease activity in a feed or a food sample including 1) a substrate for a protease activity to be measured, wherein the substrate is insoluble in aqueous solution and has a polypeptide attached to a signal producing group such that the signal is produced upon cleavage of the polypeptide by the protease; a reaction buffer essentially free of phosphate; and 3) an instruction manual for incubating the substrate with a feed sample having the protease activity to be measured, the instruction manual consisting of the steps of a) adding the substrate for the protease to the feed sample; b) mixing the substrate with the feed sample one or more times; c) incubating the substrate with the feed sample in the reaction buffer essentially free of phosphate under conditions that allow for cleavage of the polypeptide such that the signal is produced for measurement of the protease activity; and d) qualitatively, semi-quantitatively, or quantitatively measuring the protease activity by the amount of the signal that is produced.

Thus, the kits of the present disclosure do not require centrifugation or filtration of the sample to separate the reaction buffer from the feed or food sample in order to obtain a measurement of the protease activity in the sample. This allows for the assay to be performed using the kit without the use of expensive equipment. In addition, the present kits for measuring protease assay can be used at the site of feed/food processing, obviating the need to ship the samples off-site for analysis and, thus, avoiding lengthy delays in obtaining sample results.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Unexpected Discovery of Phosphate Interference with In-Feed Protease Assay

While attempting to measure the amount of protease that had been previously added to a sample of animal feed, the present inventors discovered the unexpected result that the phosphate buffer widely used to measure the protease activity was interfering with the activity measurement in the presence of the feed. The present inventors discovered that protease activity could be measured in the presence of feed when the buffer used was free of phosphate. These striking results are shown in FIGS. 1 and 2. FIG. 1 shows protease activity (300

U/g VERSAZYME/CIBENZA DP100, BIORESOURCE, INC) measured in the presence and absence of feed in a phosphate containing buffer. The proease activity assay used in FIG. 1 was performed by massing 3.5 g of feed into a conical 50 mL test tube, adding the VERSAZYME protease enzyme, resuspending the feed in 16 mL of 200 mM Na—$PO_4$ buffer, pH9.0, containing one tablet (100 mg) of PROTAZYME AK substrate cat #I-AZCAS, MEGAZYME, INC), and incubating overnight at 50° C. temperature. The PROTAZYME AK substrate is insoluble in aqueous solutions and comprises casein protein linked to azurine. Thus, cleavage of the PROTAZYME AK substrate results in the production of a green-blue color which can be observed visually or quantified by reading the absorbance of the sample supernatant at 590 nm. As can be seen in FIG. 1, there appears to be close to a complete absence of protease activity in the sample containing feed, whereas there is a large amount of protease activity in the sample without feed.

Before the discovery disclosed herein, the negative results observed in the presence of feed (as exemplified in FIG. 1) were believed to be due to competition of endogenous protein substrates in the feed. The results described herein below and shown in FIG. 2 indicate that this is not the case. FIG. 2 shows the results for the protease activity assay in the presence of feed when a 200 mM Tris-Cl buffer, pH9.0 is used in place of the phosphate buffer (1000 U/g VERSAZYME enzyme was used for this experiment). Surprisingly, and unlike for use of a phosphate buffer, the Tris buffer results in an easily identifiable positive signal in the presence of feed (see FIG. 2).

In addition, a significant reduction in the reaction signal was observed when a small quantity of phosphate was added to the Tris buffer in the same reaction described for FIG. 2 (buffer conditions were 97.5% 200 mM Tris-Cl pH9.0 and 2.5% 200 mM Na—$PO_4$ pH9.0) (results not shown). The reaction signal decreased visibly in the presence of 2.5% Na—$PO_4$ buffer. Without being bound to any one theory of mechanism, these results indicate that the negative results observed with use of phosphate buffer are due to a negative interference of phosphate with the feed rather than competition of endogenous protein substrates in the feed as is commonly believed by those of skill in the field.

The discovery that phosphate interferes with measurement of protease activity in feed was such an unexpected result, because there is a commonly held belief in the field that the protein components of the feed are what are interfering with the measurement. It is generally thought that certain of the protein components of the feed serve as competing substrates with the added labeled substrate for the protease being measured. For example, the manufacturer of the PROTAZYME AK substrate for use in measuring protease activity stated the following in a publication of frequently asked questions: "Q. 3: Is it possible to perform "in feed" determination with the Protazyme AK tablets (neutral and/of acidproteases)? A: It is difficult to determine protease in food samples because these contain a lot of endogenous protein which acts as an alternative substrate. This is a problem independent of which assay procedure you employ." (see http://secure.megazyme.com/files/FAQ%27s/T-PRAK1000_1204_FAQ.pdf).

Example 2

In-Feed Protease Assay in Phosphate Free Buffer

Detergent Concentration

It was desired to develop an assay for protease activity in the presence of a complex sample, such as an animal feed or a food, which could be performed on site, in a relatively short amount of time, and that would not require expensive instrumentation. The following experiments were performed to determine the amount of detergent to include in the assay.

The following experiments were performed to determine the effect of detergent type and concentration on the in-feed protease assay. In the first experiment 3.5 g of a mash type of feed was massed into a conical 50 mL test tube, dosed with the VERSAZYME enzyme (0, 123, 243, 359 or 471 U/g), resuspended in 16 mL of 200 mM Tris-Cl pH9.0 containing 1% sodium dodecyl sulfate (SDS) containing the PROTAZYME AK substrate (100 mg), and incubated at 50° C. for 2 hr (see Table I). The results show that the addition of 1% SDS significantly reduced the assay time to approximately 2 hr at 50° C. in the mash feed. These assay conditions are robust enough to detect VERSAZYME enzyme concentrations as low as 125 U/g, which is less than half a typical dose added to feed. Equally important is the minimal background that was observed with the control feed (results not shown). Such low background allows for easy identification of a positive signal and can allow for elimination of the need for control feed in the finished assay. This is an especially important point as control feeds are often not available once pellet mills start incorporating the protease enzyme into the feed. Further studies were conducted with the mash feed in the laboratory with each producing a consistently strong positive reaction (data not shown).

TABLE I

In-Feed Assay at 50° C., 2 hr, 1% SDS

| Sample (Mashed Feed) | VERSAZYME (U/g) | Reaction |
|---|---|---|
| 1 | 0 | Negative |
| 2 | 123 | Positive |
| 3 | 243 | Positive |
| 4 | 359 | Positive |
| 5 | 471 | Positive |

The experiment described above was repeated using pelleted feed in place of the mash feed. A pelleting run was conducted at the NC STATE BLISS PELLET MILL to obtain pelleted feed. The initial analysis of this pelleted feed did not result in a robust signal for protease activity as was observed for the mash feed (data not shown). In an effort to overcome the limited response, increasing concentrations of SDS were incorporated into the assay buffer.

The pelleted feed was analyzed in a 200 mM Tris-Cl, pH9.0, buffer supplemented with 1%, 2%, 3%, 4%, or 5% SDS and the samples were incubated at 50° C. for up to 3 hr. The results for the 1% SDS and 5% SDS samples are provided below in Table II. The sample labeled "(−) Ctrl" is feed without added VERSAZYME protease, the sample labeled "Sample" is feed to which 389 U/g of the VERSAZYME protease was added prior to the pelleting process, and the sample labeled "(−) Ctrl+VZ" was feed spiked with 350 U/g VERSAZYME protease after the pelleting process. The data indicate that increasing the SDS concentration to 5% in the assay buffer produced an easily identifiable signal for both the Sample and (−) Ctrl+VZ samples within 2 hr at 50° C. The amount of VERSAZYME protease activity detected for the Sample was 271 U/g (data not shown). Importantly, the increased SDS concentration did not increase the background signal in the control feed without added protease (data not shown).

TABLE II

In-Feed Assay at 50° C., 1.5 hr, 1% to 5% SDS

| Sample (Pelleted Feed) | Added VERSAZYME (U/g) | Reaction (5% SDS) | Reaction (1% SDS) |
|---|---|---|---|
| (−) Ctrl | 0 | Negative | Negative |
| Sample | 389 | Positive | Negative |
| (−) Ctrl + VZ | 350 | Positive | Positive |

The experiment described above was repeated using pelleted feeds from various sources. Three different wheat based pelleted feed samples (pelleting at 65° C.) were obtained from NOVUS INTERNATIONAL for analysis. Using the same assay conditions (+5% SDS) as described above for the NC STATE BLISS MILL pelleted feed resulted in an easily identifiable signal after incubation for 45 min at 50° C. (see Table III below). These results demonstrate the reproducibility of the protease assay with a variety of pelleted feeds.

TABLE III

In-Feed Assay at 50° C., 45 min, 5% SDS

| Pelleted Feed from 3 Separate Sources | Added VERSAZYME | Reaction |
|---|---|---|
| Ctrl | No | Negative |
| 1 | Yes | Positive |
| 2 | Yes | Positive |
| 3 | Yes | Positive |

The protease assay experiment described above was repeated at 30° C., but a robust signal was not produced at this lower temperature. In order to optimize the conditions for performing the in-feed protease activity assay at temperatures closer to room temperature, the protease assay was repeated using higher detergent concentrations. The SDS concentrations tested were 5, 7.5, 10, and 15% (200 mM Tris-Cl, pH 9.0). The NC STATE BLISS MILL and NOVUS INTERNATIONAL pelleted feed samples both produced a visually identifiable signal at the 10% and 15% SDS concentrations within a 4 hr incubation period at 30° C. (data not shown).

The protease assay experiment described above was repeated using Tween 20, Tween 80, or Triton X-100 in place of SDS. The experiment was performed as described previously using NC STATE BLISS PELLET MILL TURKEY PELLET feed, 350 U/g VERSAZYME protease, 0%, 1%, 5% or 10% of one of Tween 20, Tween 80, or Triton X-100 and incubated at 50° C. for up to 5 hr. In addition, a positive control sample containing 5% SDS was included in the experiment. None of the Tween 20, Tween 80, or Triton X-100 detergents produced a significant signal even after 5 hr at 50° C. (data not shown). In comparison, the 5% SDS control sample produced a strongly positive reaction (data not shown).

Example 3

In-Feed Protease Assay in Phosphate Free Buffer pH and Buffer Studies

Because the optimum pH activity for VERSAZYME protease is between 10 and 11 it was hypothesized that increasing the pH of the protease assay buffer would increase the signal response and allow for a reduction in incubation time. The in-feed protease activity assay was repeated as described above at 50° C. for 120 min using each of the following buffers supplemented with 10% SDS: 200 mM Tris-Cl pH 9.0, 200 mM $Na_2CO_3$ pH 9.0, 200 mM $Na_2CO_3$ pH 10.0, and 200 mM $Na_2CO_3$ pH 10.8. The final pH of each of the resuspended samples was measured and is shown below in Table IV. In contrast to the expected increase in protease activity, this set of buffers and an increase in sample pH had an adverse impact on measured protease activity (see Table V). In addition, the Tris-Cl pH 9.0 buffer out-performed the $Na_2CO_3$ buffers at all pH values tested (data not shown).

TABLE IV

In-Feed Assay Evaluation of Buffer pH

| Buffer | Expected pH | Observed pH | pH Difference |
|---|---|---|---|
| TRIS | 9.0 | 7.54 | 1.46 |
| $Na_2CO_3$ | 9.0 | 7.03 | 1.97 |
| $Na_2CO_3$ | 10.0 | 8.2 | 1.8 |
| $Na_2CO_3$ | 10.8 | 9.04 | 1.76 |

TABLE V

In-Feed Assay with Various Buffers and pH

| Pelleted Feed Sample | Added VERAZYME (U/g) | Reaction Tris pH 9.0 | Reaction $Na_2CO_3$ pH 9.0 | Reaction $Na_2CO_3$ pH 10.0 | Reaction $Na_2CO_3$ pH 10.8 |
|---|---|---|---|---|---|
| 1 | 0 | Negative | Negative | Negative | Negative |
| 2 | 175 | Positive | Positive | Negative | Negative |
| 3 | 262.5 | Positive | Positive | Negative | Negative |
| 4 | 350 | Positive | Positive | Positive | Negative |
| 5 | 462.5 | Positive | Positive | Positive | Negative |

A similar experiment was performed to test the effects of using glycine buffers at pH 9.0 and higher and Tris-Cl pH 9.0 buffers having increased molarity. The in-feed protease activity assay was repeated as described above at 30° C. for 2.5 hr with periodic shaking to mix contents using each of the following buffers supplemented with 10% SDS: 200 mM Tris-Cl pH 9.0, 0.5M Tris-Cl pH 9.0, 0.5M Glycine pH 9.0, or 0.5M Glycine pH 10.6. Surprisingly the 200 mM and 0.5M Tris-Cl buffers produced very similar results to one another (data not shown). Both Tris buffers outperformed the glycine buffers analyzed (data not shown).

Another similar experiment was performed to test the effects of using CAPSO, CAPS, CHES, and Citrate buffers at both high and low pH. The in-feed protease activity assay was repeated as described above at 50° C. with shaking every 15 min using each of the following buffers supplemented with 5% SDS: 200 mM CAPSO pH 9.0 and 10.0, 200 mM CAPS pH 9.0 and 10.0, CHES pH 9.0 and 10.0, or Citrate pH 3.0 and 4.0. The CHES, CAPSO, and CAPS buffers all produced easily identifiable responses at both pH 9.0 and 10.0 (see Table VI below). The protease activity response was better at pH 9.0 than at higher pH's. This is surprising since the VERSAZYME protease has greater specific activity at more alkaline pH levels. The low pH Citrate buffer did not produce any identifiable reaction even after 3 hr at 50° C. (data not shown).

TABLE VI

In-Feed Assay with CHES, CAPSO, and CAPS Buffers

| Pelleted Feed Sample | Added VERAZYME (U/g) | CHES pH 9.0 | CHES pH 10.0 | CAPSO pH 9.0 | CAPSO pH 10.0 | CAPS pH 9.0 | CAPS pH 10.0 |
|---|---|---|---|---|---|---|---|
| 1 | 0 | Negative | Negative | Negative | Negative | Negative | Negative |
| 2 | 350 | Positive | Positive | Positive | Positive | Positive | Positive |

Example 4

In-Feed Protease Assay in Phosphate Free Buffer

Quantitative and Visually Qualitative Response of Assay

The linearity of the response of the protease assay was determined using the PROTAZYME AK substrate and a corn-based mash feed according to the general procedure described in Example 1. A range of PROTAZYME AK substrate concentrations (10, 25, 50 and 100 mg) were investigated with incubation at 50° C. to determine the amounts that would provide a linear response for protease activity spectrophotometrically and that could also be qualitatively quantified visually. Specifically, 3.5 g of the feed was added to 50 mL conical tubes containing 10, 25, 50, or 100 mg of the PROTAZYME AK substrate. The samples were spiked with VERSAZYME protease enzyme resuspended in 200 mM Tris pH9.0, 1% SDS to achieve a standard curve with 0, 175, 262.5, 350, and 462.5 units of protease activity per gram of feed. The samples were then resuspended in a final volume of 20 ml of 200 mM Tris pH 9.0, 1% SDS and incubated at 50° C. for 90 min.

Figure 3A:
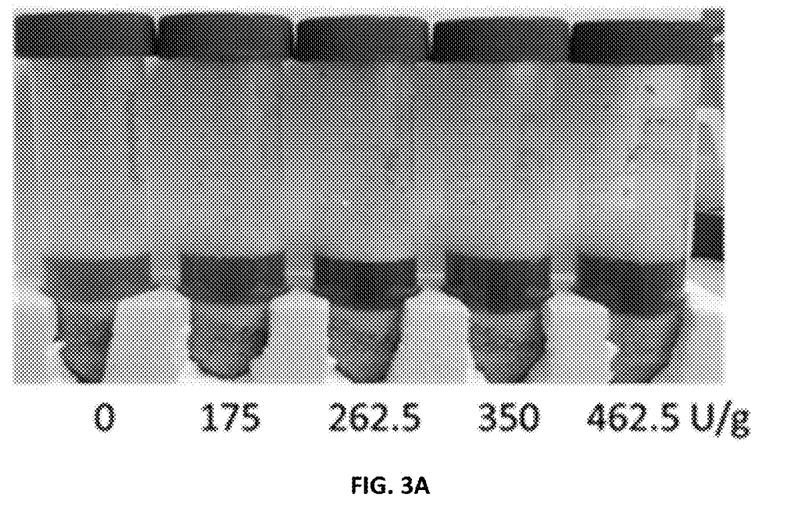
FIGS. 3A-3D are a photograph (3A) and graphical representations (3B-3D) of the color response produced by the in-feed protease assay with increasing concentrations of protease using 4 different amounts of PROTAZYME AK substrate.
Figure 3B:
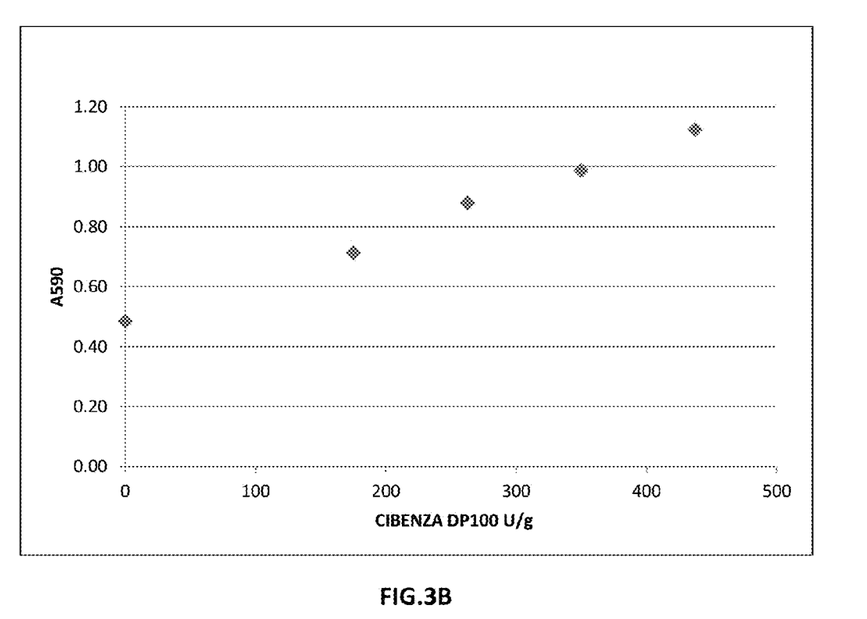
Figure 3C:
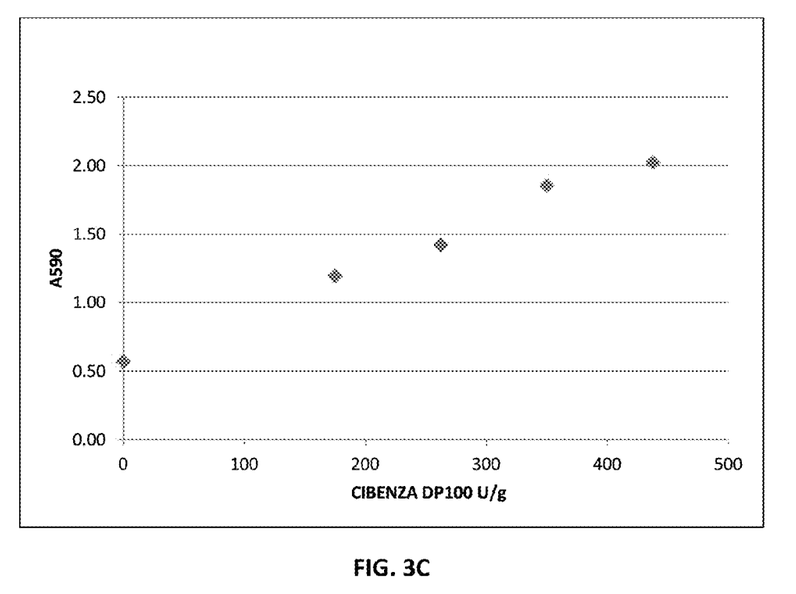
Figure 3D:
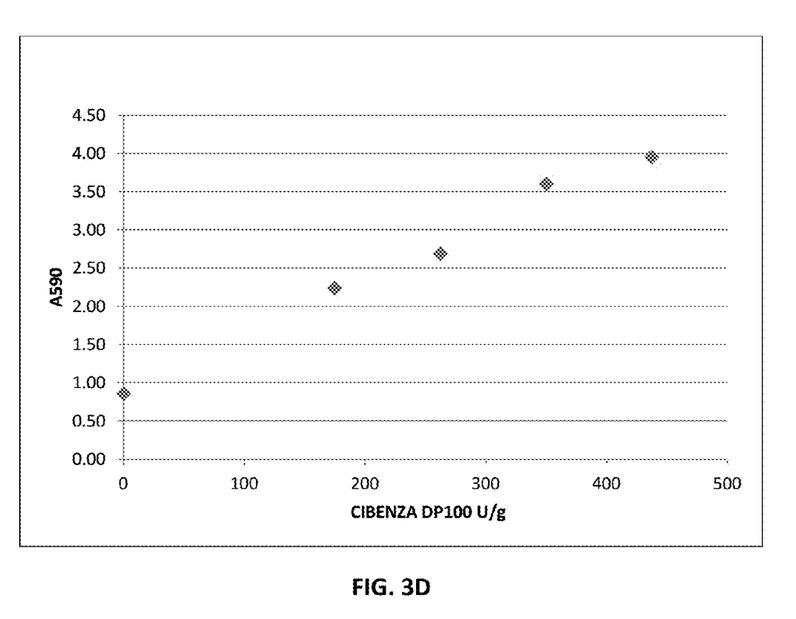

After the 90 min incubation, the samples were inspected visually. FIG. 3A is a photograph of the experimental samples using the 10 mg amount of the PROTAZYME AK substrate. Under the conditions tested, the 10 mg substrate concentration allowed for the best visual inspection of response, although the 10 mg amount of substrate did not produce an ideal spectrophotometric response. In addition to visual inspection, 1.5 mL of each sample was removed and centrifuged at 3,500×g for 5 min to pellet the insoluble feed fraction of the sample. The resulting supernatant was diluted either 2-fold or 4-fold and the absorbance read at $A_{590}$. The data show a spectrophotometric linear response for each of the 25, 50, and 100 mg substrate concentrations (see FIGS. 3B-3D, respectively). Thus, the in-feed protease assay can be used to allow for a visual inspection of response as well as to produce a linear response to increasing protease concentrations.

Figure 4:
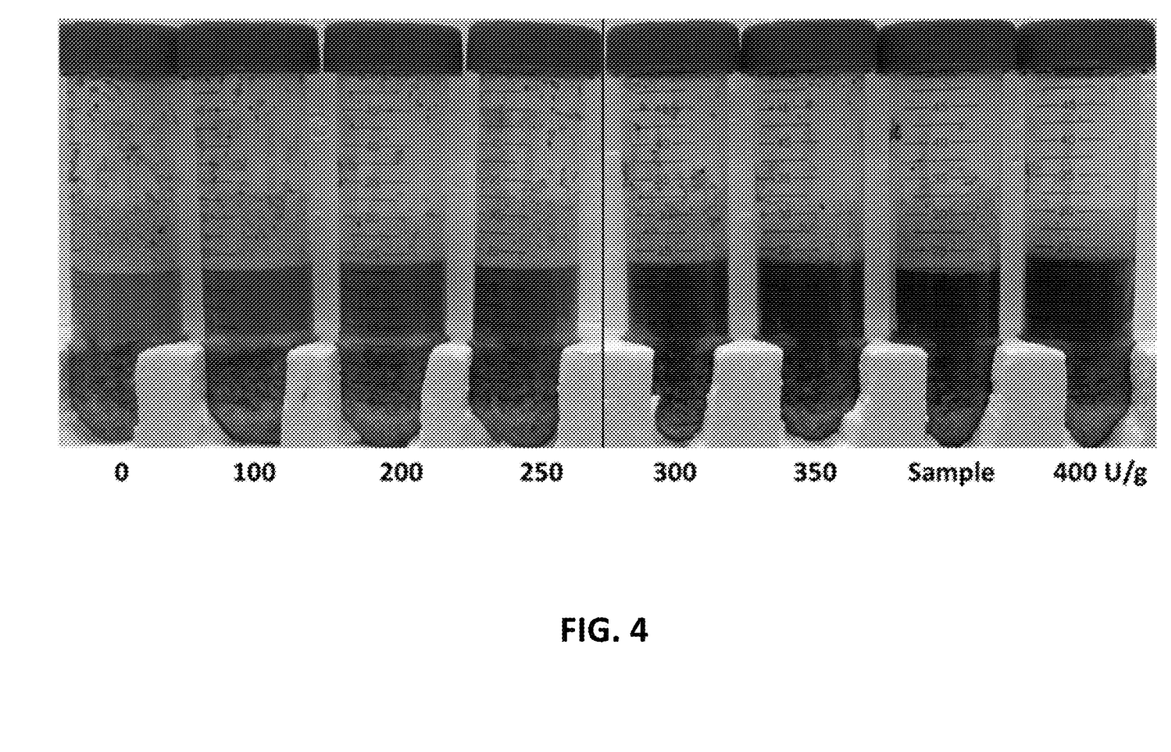
FIG. 4 is a photograph of the visual color response produced by the in-feed protease assay with increasing concentrations of protease using 100 mg of PROTAZYME AK substrate in 200 mM Tris-Cl, pH 9.0, containing 5% SDS, at 40° C. Each tube contained 3.5 g of pelleted feed to which the designated amount of protease activity (U/g) was added after feed pelleting. The tube marked "Sample" contained 389 U/g activity of the protease added prior to feed pelleting.

In a similar experiment in pelleted feed, a standard curve of VERSAZYME protease enzyme ranging from 0 to 400 U/g was prepared in pelleted feed and the protease assay performed as described above using 100 mg PROTAZYME AK substrate in 20 mL of 200 mM Tris-Cl, pH 9.0, containing 5% SDS, at 40° C. As an additional control, a feed sample dosed at 389 U/g VERSAZYME protease enzyme prior to feed processing ("Sample") was included in this examination. As indicated in FIG. 4, the standard curve allows for easy visual identification of differences between 0, 100, 200, 250, 300 and 350 U/g of the protease enzyme. The color only appears to start saturating at the 350 to 400 U/g concentrations. Based on this standard curve the Sample is easily identified as containing greater than 350 U/g protease enzyme.

Based on these results, the protease assay can be useful for quantitatively measuring protease activity by measuring the absorbance at 590 nm in the soluble fraction of a feed sample. In addition, the protease assay can be useful for qualitatively assessing the amount of protease activity in a feed sample by visual inspection of the feed sample without the need for a centrifugation or filtration step to separate the soluble and insoluble fractions and without the need for a spectrophotometer to measure an absorbance value.

Example 5

In-Feed Protease Assay in Phosphate Free Buffer

Other Commercial Feed Proteases

The in-feed protease assay was tested for proteases other than the VERSAZYME protease that are commercially available for addition to feed. Specifically, feed proteases RONOZYME PROACT (DSM, INC.) and AXTRA 102 TPT XAP (DANISCO, INC.) were examined. For this protease assay, increasing concentrations of SDS ranging from 0.1% to 5% were examined due to concerns of enzyme stability in this detergent. The protease assay was performed according to the following description for each of the enzymes. First, 3.5 g of mash-type feed was massed into a 50 mL centrifuge tube, PROTAZYME AK substrate was added (100 mg), and then 20 mL of 200 mM Tris-Cl pH9.0 containing SDS (0.1%, 0.5%, 1%, 2%, 5%, or 10% SDS) was added to individual samples.

VERSAZYME Protease Enzyme:

100 mg of VERSAZYME protease enzyme was diluted into 40 mL of 200 mM Tris-Cl pH 9.0 and 710 μL of the enzyme dilution was spiked onto the feed samples (roughly 350 U/g of feed).

AXTRA XAP Protease Enzyme:

20 mg of AXTRA XAP was diluted into 10 mL of 200 mM Tris-Cl pH9.0 and 482 μL of the enzyme dilution was spiked on top of the feed samples, the same dosage level suggested by the manufacturer (250 g/ton feed).

RONOZYME PROACT Protease Enzyme:

20 mg of RONOZYME PROACT was diluted into 10 mL of 200 mM Tris-Cl pH9.0 and 385 μL of the enzyme dilution was spiked on top of feed, the same dosage level suggested by the manufacturer (200 g/ton feed).

Each of the samples was then incubated at 50° C. in a water bath for 1.75 hr. Samples were mixed with vigorous shaking every 10 min and checked for color development. Both the RONOZYME PROACT and AXTRA 102 TPT protease enzymes performed well in this assay with the best color development in 5% SDS. In addition, even at the highest 10% SDS concentration, both RONOZYME PROACT and AXTRA 102 TPT exhibited a high level of color development. These results indicate that the in-feed protease assay of the present disclosure can be useful for measuring activity of proteases that are added to feed other than the VERSAZYME protease.

Example 6

In-Feed Protease Assay in Phosphate Free Buffer

Temperature Studies

The following experiments were performed to determine the conditions for performing the in-feed protease assay at room temperatures. For these experiments 3.5 g of pelleted feed (NC STATE BLISS PELLET MILL TURKEY PELLET) was used with 100 mg PROTAZYME AK substrate. The feed samples (control without added protease, +300 U/g VERSAZYME, +RONOZYME PROACT (200 g/ton feed), or +AXTRA XAP 102 TPT (250 g/ton feed)) were resuspended in 20 mL of 200 mM Tris pH9.0 containing SDS (0%, 0.5%, 1%, 5%, or 10% SDS) in a 50 mL centrifuge tube. Sample was mixed by shaking every 15 min and incubated at various temperatures (20° C., 60° C., and 65° C.) until color developed for up to five hours.

The results for the three proteases at 20° C., 60° C., and 65° C. are shown in Tables VII-IX below. Only a negligible signal was observed for each of the three enzymes when incubated at 20° C. for 4.75 hr even at the highest SDS concentrations, while all of the enzymes produced an obvious signal at 60° C. and 65° C.

TABLE VII

In-Feed Assay for VERSAZYME at Various Temperatures and 5% SDS

| Pelleted Feed Sample | Added VERSAZYME (U/g) | Reaction at 20° C. | Reaction at 60° C. | Reaction at 65° C. |
|---|---|---|---|---|
| 1 | 0 | Negative | Negative | Negative |
| 2 | 350 | Negative | Positive | Positive |

TABLE VIII

In-Feed Assay for AXTRA XAP 102 TPT at 20° C. and Varying Detergent Concentration

| Pelleted Feed Sample | Added AXTRA XAP 102 TPT (g/ton) | Reaction SDS 0% | Reaction SDS 0.5% | Reaction SDS 1% | Reaction SDS 5% | Reaction SDS 10% |
|---|---|---|---|---|---|---|
| 1 | 0 | Negative | Negative | Negative | Negative | Negative |
| 2 | 250 | Negative | Negative | Negative | Negative | Negative |

TABLE IX

In-Feed Assay for RONOZYME PROACT at 20° C. and Varying Detergent Concentration

| Pelleted Feed Sample | Added RONOZYME PROAVT (g/ton) | Reaction SDS 0% | Reaction SDS 0.5% | Reaction SDS 1% | Reaction SDS 5% | Reaction SDS 10% |
|---|---|---|---|---|---|---|
| 1 | 0 | Negative | Negative | Negative | Negative | Negative |
| 2 | 200 | Negative | Negative | Negative | Negative | Negative |

Example 7

In-Feed Protease Assay in Phosphate Free Buffer

Non-Feed Proteases

In order to determine whether the in-feed protease assay is functional for a wide spectrum of proteases, the enzymes pepsin, subtilisin, trypsin, chymotrypsin, and proteinase K were tested in the assay.

Pepsin:

Pepsin was tested with the in-feed protease assay using 100 mg PROTAZYME AK substrate and incubating at pH 1.0 in the presence of 0%, 0.1%, 0.5%, 1% and 5% SDS at 40° C. for 2 hours. Specifically, 3.5 g of NC STATE BLISS PELLET MILL TURKEY PELLET was ground to a fine powder and massed into a 50 mL conical tube. 80 mg of pepsin (SIGMA P7124-100G Lot#049K1003@118 U/mg solid) was dosed at a 0.4% enzyme ratio to feed. Samples were resuspended in 20 mL of $dH_2O$ and pH was adjusted to 1, 2, 3, and 4 with the addition of 12M HCl. SDS was added at each pH at 0%, 0.1%, 0.5%, 1%, and 5% (w/v). Samples were then mixed by vigorous shaking and incubated at 40° C. until color development, or until the maximum 4 hr incubation.

As indicated in Table X below, pepsin produced a strong reaction at pH 1 and 0% SDS. This result demonstrates that pepsin activity can be measured using this protease assay.

TABLE X

In-Feed Assay for Pepsin at pH 1.0 and Varying Detergent Concentration

| Feed Sample | Pepsin (U/mg) | % SDS | Reaction |
|---|---|---|---|
| 1 | 118 | 0 | Positive |
| 2 | 118 | 0.1 | Positive |

TABLE X-continued

In-Feed Assay for Pepsin at pH 1.0 and Varying Detergent Concentration

| Feed Sample | Pepsin (U/mg) | % SDS | Reaction |
|---|---|---|---|
| 3 | 118 | 0.5 | Negative |
| 4 | 118 | 1 | Negative |
| 5 | 118 | 5 | Negative |

Subtilisin, Trypsin, and Chymotrypsin:

Subtilisin, trypsin, and chymotrypsin were tested with the in-feed protease assay using 100 mg PROTAZYME AK substrate. Specifically, 3.5 g of NC STATE BLISS PELLET MILL TURKEY PELLET was ground to a fine powder and massed into a 50 mL conical tube. Subtilisin (SIGMA P5380-100MG Lot#119K1088V @ 67,000,000 U/g), chymotrypsin (SIGMA C3142-25MG Lot#041M7012V@20,000,000 U/g), trypsin (SIGMA T1426-250MG Lot#SLBB9512V@90,000,000 U/g), and VERAZYME 700,000 U/g were added to feed at a final concentration of 350 U/g. Samples were resuspended in 20 mL of 200 mM Tris pH9.0. SDS was added to each sample at 0%, 0.1%, 1%, and 5% SDS. Samples were mixed by vigorous shaking and incubated at 50° C.

The data for subtilisin, trypsin, and chymotrypsin with the in-feed protease assay are shown in Table XI. As indicated by the data, subtilisin is compatible with the in-feed protease assay. A strong signal was observed with this protease at 1% and 5% SDS. As indicated in Table XI, trypsin and chymotrypsin are not compatible with the protease assay failing to produce an identifiable signal under any of the tested conditions.

XI. In-Feed Assay for Different Proteases

| Feed Sample | Protease (U/g) | % SDS | Reaction VERSAZYME | Reaction Subtilisin | Reaction Trypsin | Reaction Chymotrypsin |
|---|---|---|---|---|---|---|
| 1 | 0 | 0 | Negative | Negative | Negative | Negative |
| 2 | 350 | 0.1 | Negative | Negative | Negative | Negative |
| 3 | 350 | 0.5 | Negative | Negative | Negative | Negative |
| 4 | 350 | 1 | Positive | Positive | Negative | Negative |
| 5 | 350 | 5 | Positive | Positive | Negative | Negative |

Proteinase K:

Proteinase K was tested with the in-feed protease assay at high pH values using 100 mg PROTAZYME AK substrate. Specifically, 3.5 g of NC STATE BLISS PELLET MILL TURKEY PELLET was ground to a fine powder and massed into a 50 mL conical tube. Proteinase K (FISHER Product #BP1700-100 Lot #051308@100,000,000 U/g), was added to feed at a final concentration of 350 U/g. Samples were resuspended in 20 mL of 200 mM Tris-Cl pH9.0, 200 mM CAPS pH10 and pH11, 200 mM KCl—NaOH pH12, or by addition of NaOH to adjust the pH to pH10, pH11, and pH12. Upon addition of the indicated buffer to feed samples the pH was verified, and where needed, NaOH was added in order to obtain the indicated pH of each buffer. SDS was added to samples at 0%, 0.1%, 1% and 5% SDS. Samples were then mixed by vigorous shaking and incubated at 50° C.

The data for Proteinase K with the in-feed protease assay are shown in Table XII. As indicated in Table XII, Proteinase K is compatible with the in-feed protease assay. The upper limit for SDS concentration for Proteinase K was determined to be 1% SDS and the upper pH for Proteinase K is pH 9.0.

TABLE XII

In-Feed Assay for Proteinase K

| Feed Sample | Proteinase K (U/g) | Reaction pH 9 | Reaction pH 10 | Reaction pH 11 | Reaction pH 12 |
|---|---|---|---|---|---|
| 1 | 0 | Negative | Negative | Negative | Negative |
| 2 | 350 | Positive | Negative | Negative | Negative |

Example 8

In-Feed Protease Assay in Phosphate Free Buffer

Insoluble Casein-Remazol Brilliant Blue Substrate

The in-feed protease assay was tested using a water insoluble casein substrate rather than the PROTAZYME AK substrate. The insoluble casein substrate was generated by cross-linking gelatin to casein, as casein itself is soluble in aqueous solution. Prior to crosslinking the gelatin to the casein, the casein was labeled with Remazol Brilliant Blue (RBB) such that the proteolytic degradation of the finished gelatin-casein-RBB substrate could be monitored.

Figure 5:
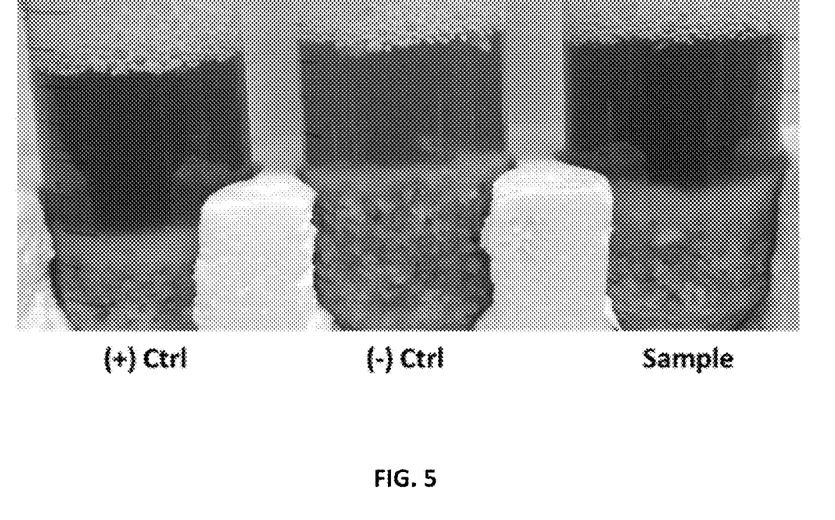
FIG. 5 is a photograph showing the visual color response produced by the in-feed protease assay using 100 mg of an insoluble casein substrate in which the casein is linked to Remazol Brilliant Blue (RBB) in 200 mM Tris-Cl, pH 9.0, containing 5% SDS, at 50° C. for 2 hr. The (−) Ctrl is feed without added VERSAZYME protease, the (+) Ctrl contains 500 U/g VERSAZYME protease added after feed processing, and the Sample contains 389 U/g VERSAZYME protease added prior to feed processing.

The in-feed protease assay was performed generally as described herein previously using 100 mg of ground gelatin-casein-RBB as the substrate for the protease VERSAZYME. Specifically, 3.5 g of mashed feed was weighed out into 50 mL conical tubes and 20 mL of 200 mM Tris-Cl pH9.0 containing 5% SDS was added to each sample. The samples analyzed were "(+) Ctrl" (feed with 500 U/g Versazyme added after feed processing), "(−) Ctrl" (feed without added VERSAZYME), and "Sample" (feed with 389 U/g Versazyme added prior to feed processing). The gelatin-casein-RBB substrate was then added to each sample and mixed by vigorous shaking. Samples were incubated at 50° C. in a water bath for 2 hr and monitored for color change over time. As shown in FIG. 5, a readily identifiable signal was observed in the feed samples containing VERSAZYME compared to the control feed without added protease.

These results indicate that the in-feed protease assay can be useful with a variety of insoluble protease substrates that contain a signal producing group such as, for example, a chromophore, a flurophore, or a radioisotope capable of producing a signal upon cleavage of the substate by the protease. Insoluble protease substrates that contain a group that produces a color change upon cleavage of the substate can be useful with the in-feed protease assay for both semi-quantitative visual inspection and for generating quantitative results by reading absorbance with a spectrophotometer.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method for measuring protease activity in a feed sample, comprising:
   a) adding a substrate for a protease to a feed sample that comprises the protease activity to be measured, wherein the substrate is insoluble in aqueous solution and comprises a polypeptide attached to a chromophore signal producing group such that the signal is produced upon cleavage of the polypeptide by the protease;
   b) incubating the substrate with the feed sample in a reaction buffer essentially free of phosphate, comprising 3% to 15% of an ionic detergent at a pH range between about pH 6.5 to pH 11, and at a temperature of about 30° C. to 65° C. for a length of time that allows for cleavage of the polypeptide such that the signal is produced for measurement of the protease activity; and
   c) measuring the protease activity by visual inspection of a color change resulting from the signal produced by the chromophore.

2. The method of claim 1, wherein the polypeptide is casein.

3. The method of claim 1, wherein the feed is an animal feed and the protease is a type of protease that is added to the animal feed to improve the protein digestability of the feed.

4. The method of claim 1, wherein the animal feed is a pelleted feed and the buffer comprises about 5% to 10% sodium dodecyl sulfate (SDS).

5. The method of claim 1, wherein the reaction buffer is a Tris buffer at a pH of about pH7 to pH9.

6. A method for measuring protease activity in a feed sample, consisting of:
   a) adding a substrate for a protease to a feed sample that comprises the protease activity to be measured, wherein the substrate is insoluble in aqueous solution and comprises a polypeptide attached to a signal producing group such that the signal is produced upon cleavage of the polypeptide by the protease;
   b) mixing the substrate with the feed sample one or more times;
   c) incubating the substrate with the feed sample in a reaction buffer essentially free of phosphate, comprising 3% to 15% of an ionic detergent at a pH range between about pH 6.5 to pH 11, and at a temperature of about 30° C. to 65° C. for a length of time that allows for cleavage of the polypeptide such that the signal is produced for measurement of the protease activity; and
   d) qualitatively, semi-quantitatively, or quantitatively measuring the protease activity by the amount of the signal that is produced.

7. The method of claim 6, wherein the polypeptide is casein and the signal producing group is one of a chromophore, a flurophore, or a radioisotope.

8. The method of claim 6, wherein the signal producing group is a chromophore, and wherein the measuring is through visual inspection of a color change resulting from the signal produced by the chromophore.

9. The method of claim 6, wherein the feed is an animal feed and the protease is a type of protease that is added to the animal feed to improve the protein digestability of the feed.

10. The method of claim 6, wherein the animal feed is a pelleted feed and the buffer comprises about 5% to 10% sodium dodecyl sulfate (SDS).

11. The method of claim 6, wherein the reaction buffer is a Tris buffer at a pH of about pH7 to pH9.

* * * * *